United States Patent [19]

Schmukler

[11] Patent Number: 4,648,384
[45] Date of Patent: Mar. 10, 1987

[54] RETROGRADE CORONARY SINUS PERFUSION DEVICE AND METHOD

[76] Inventor: Robert E. Schmukler, 159-34 Riverside Dr. W., Apt. #4D, New York, N.Y. 10032

[21] Appl. No.: 673,793

[22] Filed: Nov. 21, 1984

[51] Int. Cl.$^4$ ............................................. A61B 19/00
[52] U.S. Cl. .................... 128/1 D; 604/53; 604/4; 604/101; 604/118; 604/254
[58] Field of Search ............... 128/1 D, 325, 207.15, 128/DIG. 3; 604/49, 52, 53, 67, 101, 127, 140, 183, 186, 246, 254, 5, 118

[56] References Cited

U.S. PATENT DOCUMENTS

| | | | |
|---|---|---|---|
| 2,854,982 | 10/1958 | Pagano | 604/101 |
| 3,543,752 | 12/1970 | Hesse et al. | 604/127 |
| 3,911,898 | 10/1975 | Leachman Jr. | |
| 3,939,820 | 2/1976 | Grayzel | 128/1 D |
| 3,983,879 | 10/1976 | Todd | |
| 4,014,317 | 3/1977 | Bruno | |
| 4,080,958 | 3/1978 | Bregman et al. | |
| 4,183,102 | 1/1980 | Guiset | 604/101 |
| 4,245,622 | 1/1981 | Hutchins, IV | |
| 4,250,872 | 2/1981 | Tamari | 128/1 D |
| 4,314,550 | 2/1982 | Apstein | |
| 4,327,709 | 5/1982 | Hanson et al. | |
| 4,328,820 | 5/1982 | Serur | 604/254 |
| 4,456,000 | 6/1984 | Schjeldahl et al. | 128/1 D |
| 4,459,977 | 7/1984 | Pizon et al. | 128/1 D |
| 4,501,581 | 2/1985 | Kurtz et al. | 604/52 |
| 4,531,936 | 7/1985 | Gordon | 128/1 D |

FOREIGN PATENT DOCUMENTS 2029236  3/1980 United Kingdom.

OTHER PUBLICATIONS

Luessenhop; "Intra-Arterial Instrumentation for Neurosurgery"; Jul., 1960, p. 9.
Feola et al., "A Method of Coronary Rietroperfusion for the Treatment of Acute Myocardial Ischemia", *Cardiovascular Disease* (1978).
Poirier et al., "Drip Retrograde Coronary Sinus Perfusion . . . " *J. Thoracic & Cardiovascular Surgery,* 70, 6, 966-973 (1975).
Farcot, J. C. et al., "Synchronized Retro Perfusion of Coronary Veins for Circulatory Support of Jeopardized Ischemic Myocardium," Am. J. Card. 41, 119-201 (1978).
Farcot et al., "New Catheter-Pump System for Diastolic Synchronized Coronary Sinus Retroperfusion," Med. Progr. Technol. 8, 29-37 (1980).
Smith et al., "Reduction in Infarct Size by Synchronized Selective Coronary Venos Retroperfusion of Arterialized Blood".

*Primary Examiner*—Dalton L. Truluck
*Assistant Examiner*—Mario Costantino
*Attorney, Agent, or Firm*—Finnegan, Henderson, Farabow, Garrett & Dunner

[57] ABSTRACT

A retrograde coronary sinus perfusion device provides steady state blood flow to the coronary sinus and has a balloon set back from the catheter tip to block the coronary sinus during most of diastole to maximize retrograde perfusion. A global device seals the coronary sinus at the coronary sinus valve.

20 Claims, 10 Drawing Figures

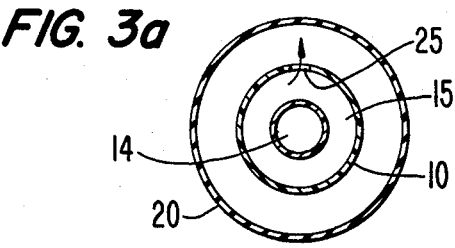
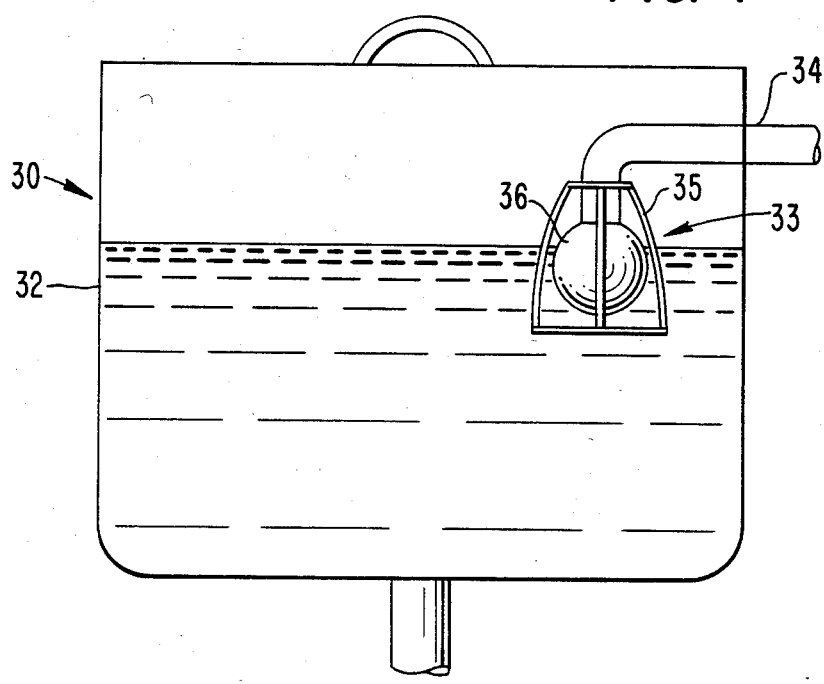
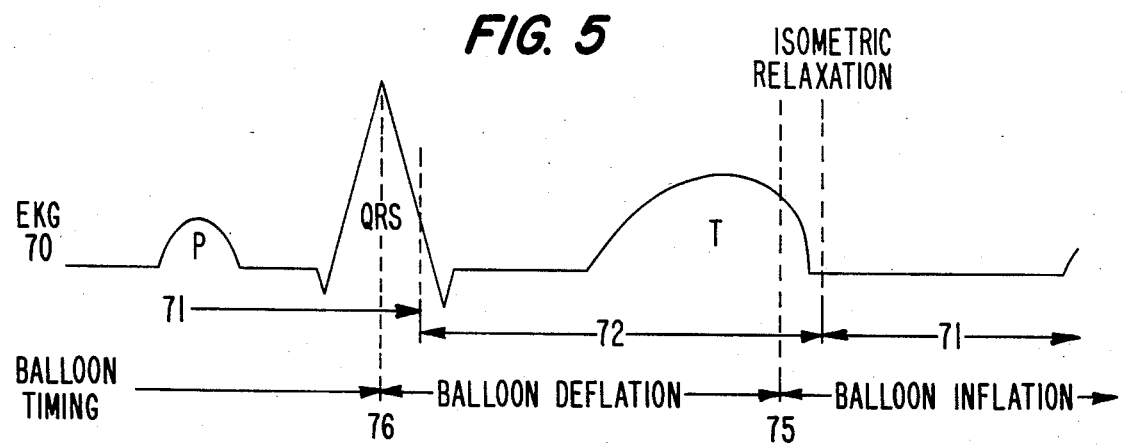

RETROGRADE CORONARY SINUS PERFUSION DEVICE AND METHOD

BACKGROUND OF THE INVENTION

This invention relates to the field of retrograde coronary sinus perfusion (RCSP) devices and methods, and more particularly to steady state RCSP devices and methods.

The primary purpose for RCSP devices is to help the victims of heart attack. During a heart attack, the coronary arteries fail to provide blood to the heart muscle. This lack of oxygenated blood causes irreversible damage to the heart if continued for too long.

To prevent or minimize the damage to the heart muscle from heart attacks, RCSP devices pump oxygenated blood, and any other drugs or nutrients deemed necessary by a doctor, to the heart muscle through the coronary veins. This is counter to the normal blood flow of the heart muscle which is usually out of those veins. In the diagram of the human heart shown in FIG. 1, an RCSP device's catheter would be inserted past coronary sinus valve 1 into coronary sinus 2. The coronary sinus is a large channel for venous blood from the heart muscles.

To operate effectively, RCSP devices must be placed into proper position in the heart very quickly because damage to heart muscles from a heart attack can occur very fast, and any time lost in positioning RCSP devices might be critical to a patient.

At present, the most common device for retrograde coronary sinus perfusion is a pulsed blood flow system which pumps blood into the heart only during the heart muscle's rest cycle or diastole. The pulsed system is inactive during the heart's pumping cycle or systole. An example of such a device is shown in Farcot, J. C., et al., "Synchronized Retro Perfusion of Coronary Veins for Circulatory Support of Jeopardized Ischemic Mycardium," *Am. J. Card.* 41, 1191–201 (1978), and GB Patent No. 2,029,236 to Durand and Farcot. Both the patent and the article describe an RCSP system having a single-lumen catheter surrounded by a balloon. The flow of blood into the catheter's lumen or channel first inflates the balloon. This blocks the coronary sinus and enhances retrograde perfusion by ensuring that the subsequent blood flowing through the catheter goes into the coronary sinus.

One problem of this and other pulsed RCSP systems is inefficiency because viscous flow damping makes it difficult to pump blood down a small diameter catheter and into the heart at the normal heart rate. It is also difficult to start and stop the flow of blood quickly because of fluid inertia. Another problem of pulsed systems is that the pumping motion of the blood produces flow shear stress which causes hemolysis which is disintegration of red blood cells.

A second type of RCSP device is a continuous or steady-state device which pumps blood continuously through a catheter in the coronary sinus. One such device, shown in Feola et al., "A Method of Coronary Retroperfusion for The Treatment of Acute Myocardial Ischemia," *Cardiovascular Disease* 5:235-2430 (1978), employs a double lumen catheter inserted into the coronary sinus. A large central lumen carries blood pumped from a blood reservoir by a roller pump to the heart. A smaller lumen is connected to a pump which inflates and deflates a balloon at the tip of the catheter in synchronism with the heart rate.

While the device in Feola et al. does not have the same problem of viscous and inertial fluid damping as pulsed RCSP systems, the roller pump still tends to damage red blood cells and, by providing constant flow, may cause harm if resistance to the blood flow into the coronary sinus increases unexpectedly. In addition, since the balloon in Feola et al. is placed at the tip of the catheter, those portions of the coronary sinus between the catheter tip and the coronary sinus valve will not receive oxygenated blood or nutrients when the balloon inflates.

Accordingly, one objective of this invention is a safe and effective RCSP device.

Another objective of this invention is a simple, efficient and reliable RCSP device that minimizes hemolysis.

Yet another objective of this invention is an RCSP device which provides oxygenated blood and nutrients to much of the heart.

SUMMARY OF THE INVENTION

To overcome the problems of the prior art and to achieve the objectives of this invention and provide its advantages, the retrograde coronary sinus perfusion device of this invention comprises: a multiple lumen catheter, a portion of which is to be inserted into the coronary sinus of a patient's heart, the catheter including first and second lumens and a tip end which is the catheter end inserted into the coronary sinus, a balloon surrounding the catheter at a distance from the catheter tip end preset to at least substantially the length of the catheter portion to be inserted into the coronary sinus, the multiple lumen catheter including a flow path between the balloon and the first lumen so gas in the first lumen may inflate the balloon, a reservoir of blood coupled to an end of the second lumen which is opposite to the tip end, the reservoir providing a supply of blood into the second lumen at a relatively constant pressure, and a balloon pump coupled to the first lumen to force gas into the first lumen at a rate synchronized with the pulse rate of the heart.

A method of this invention for retrograde coronary sinus perfusion for a patient comprises the steps of: inserting a portion of a multiple lumen catheter, tip end first, into the coronary sinus of the patient's heart; providing blood into the coronary sinus at a constant pressure; and inflating, at a rate synchronized with the pulse rate of the heart, a balloon surrounding the multiple lumen catheter at a distance from the tip end preset to substantially the length of the portion of the catheter inserted into the coronary sinus.

BRIEF DESCRIPTION OF THE DRAWINGS

FIG. 3a shows a cross section of the catheter in FIG. 3;

FIG. 4 shows a reservoir for blood used in the embodiment shown in FIG. 2;

FIG. 5 shows a representative electrocardiogram to show the timing of the retrograde coronary sinus perfusion device shown in FIG. 2;

DESCRIPTION OF THE PREFERRED EMBODIMENT

Reference will now be made in detail to presently preferred embodiments of the invention, examples of which are shown in the accompanying drawings.

Figure 1:
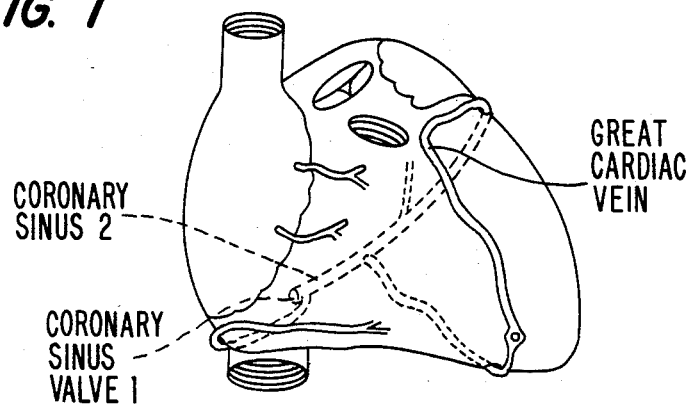
FIG. 1 is a schematic diagram of a human heart.
Figure 2:
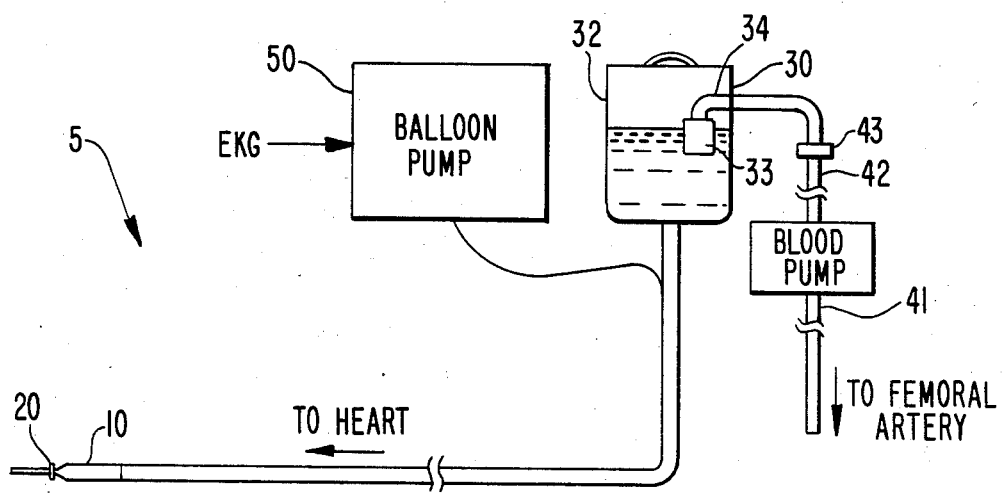
FIG. 2 shows one embodiment of a retrograde coronary sinus perfusion device of the present invention.

FIG. 2 shows one embodiment of the retrograde coronary sinus perfusion device of this invention. Device 5 includes a multiple lumen catheter 10, a balloon 20 surrounding catheter 10, a reservoir of blood 30 and a balloon pump 50. In operation, a portion of catheter 10 about twelve centimeters long is inserted into the coronary sinus of a patient's heart. In this position, balloon 20 should be one to two centimeters inside of the coronary sinus valve and be aligned with a cylindrical portion of the coronary sinus.

Figure 3:
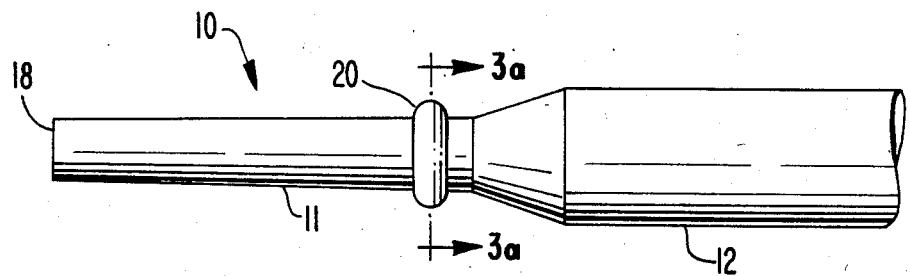
FIG. 3 shows a double lumen catheter and balloon used in the embodiment shown in FIG. 2.

As FIG. 3 shows, catheter 10 preferably has a wide portion 12 which rests outside the coronary sinus when catheter 10 is properly inserted and a narrow portion 11 which lies within the coronary sinus. Catheter portion 11 is tapered slightly from the point where it meets catheter portion 12 down to tip end 18. In the preferred embodiment of catheter 10, the tip end diameter is about two-thirds that of the coronary sinus in order to achieve the best retrograde flow and allow normal drainage.

By making the catheter portion 12 wider than portion 11, catheter 10 can be quickly and accurately positioned in patients by ensuring that portion 12 remains outside the coronary sinus.

Catheter 10 is a double lumen catheter whose cross section is shown in FIG. 3a. Inner lumen 14 is located in the center of catheter 10 and carries blood to the heart. Outer lumen 15 carries gas for inflating balloon 20.

Balloon 20 surrounds catheter 10 at a distance from tip end 18 which is substantially equal to the length of the catheter inserted into the coronary sinus, preferably about 10 centimeters. Hole 25 in catheter 10 provides a flow path between lumen 15 and balloon 20 so that gas pumped into lumen 15 enters balloon 20 and causes it to expand. Lumen 15 is sealed at the balloon to ensure that the gas in lumen 15 flows only into balloon 20 and not into the coronary sinus.

As shown in the preferred embodiment of the catheter 10 in FIG. 3, balloon 20 is also about one to two centimeters from the point where catheter portions 11 and 12 meet. This ensures that when catheter 10 is inserted into the coronary sinus, the balloon will lie one to two centimeters inside of the coronary sinus.

Lumen 14 of catheter 10 is connected to a reservoir of blood 30 which is shown in detail in FIG. 4. Reservoir 30 supplies blood through lumen 14 into the coronary sinus at a relatively constant pressure. Blood reservoir 30 includes a standard blood bag 32 to hold the blood. Bag 32 also has an atmospheric vent (not shown) for proper operation. Ball valve 33 in bag 32 keeps the blood level in bag 32 relatively constant to maintain relatively constant hydrostatic pressure on the blood into lumen 14. The pressure of the blood through lumen 14 is set by adjusting the height of bag 32. Hanging bag 32 higher increases the pressure; lowering bag 32 decreases the pressure.

The blood in reservoir 30 is preferably supplied from the patient's femoral artery. The typical blood pressure in this artery is about 100 mm Hg which is usually sufficient to pump femoral blood through catheters 41 and 42 up to bag 32. If the femoral artery pressure is insufficient, however, pump 40 can be connected to catheters 41 and 42 to force blood up to bag 32. Tubing valve 43 in catheter 42 turns on and off the supply of blood to blood bag 32.

Blood enters bag 32 from catheter 42 via tubing 34 and ball valve 33. Ball 36 in cage 35 of valve 33 has a diameter larger than that of tube 34 and can completely block tubing 34 when forced against that tubing. When the level of the blood in bag 32 rises, ball 36 is forced up until ball 36 blocks tube 34 completely. Ball 36 then prevents additional blood from entering bag 32 until the level of blood in the bag 32, and thus ball 36, drops. Ball check valve 33 thus maintains both the level of the blood in bag 32 and the hydrostatic pressure on the blood flowing into the coronary sinus relatively constant.

Ball check valve 33 also serves another purpose. Blood flowing into bag 32 from tube 34 flows first around the ball 36 contour then onto the surface of the blood in the reservoir. This prevents agitation of the blood and the formation of air bubbles in the blood and also reduces hemolysis.

If nutrients or drugs must be added to the oxygenated blood sent to the heart, such nutrients and drugs can be pumped into reservoir 32 through a ball check valve or by any other conventional means.

Balloon pump 50 shown in FIG. 2 pumps gas, preferably carbon dioxide, into and out of balloon 20 via lumen 15 of catheter 10. Pump 50 inflates and deflates balloon 20 in synchronism with the heart rate by connecting pump 50 to an electrocardiogram or to another device that monitors heart rate.

Preferably pump 50 begins to inflate balloon 20 slightly before systolic contraction ends or just before the myocardium completely relaxes. FIG. 5 shows, on a typical electrocardiogram (EKG) 70, the timing of the RCSP of this invention. Region 71 represents the diastolic or rest cycle of a heart and region 72 represents the systolic or pumping cycle of a heart. Point 75 in EKG 70 represents the approximate point to begin balloon inflation. Pump 50 deflates balloon 20 just prior to the end of diastole point 76 in FIG. 5.

The RCSP device shown in FIGS. 2-4 provides a continuous or steady-state flow of oxygenated blood and nutrients into the coronary sinus by maintaining a relatively constant hydrostatic head in blood reservoir 30. While balloon 20 is deflated, the oxygenated blood and nutrients admix with the venous blood flowing from the heart.

When pump 50 inflates balloon 20 slightly before the end of systolic contraction, a slight negative pressure appears in the cardiac venous vasculature or vein system which enhances the retrograde blood flow during diastole. During diastole, the blood from reservoir 30 flows through the coronary sinus to provide the heart with oxygen and whatever nutrients or drugs are added to the blood in reservoir 30.

Balloon 20 remains inflated until just prior to the end of diastole. It is then deflated for most of the heart's systolic contraction to allow normal drainage of the heart.

The pressure of balloon 20 is set to the level of the hydrostatic head of the blood reservoir 30 to prevent heart damage. Thus, the sinus pressure will remain at or below the balloon set pressure. If the pressure in the coronary sinus exceeds the balloon set pressure, the seal between the balloon and the sinus will leak. Also, the sinus blood will be driven back into reservoir 30 until the hydrostatic pressure equals the sinus pressure. Thus reservoir 30 also provides a sink for sinus blood and relieves coronary sinus pressure.

In the RCSP device in FIGS. 2-4, the balloon is set about 10 centimeters from the catheter tip end so that when the balloon inflates, the oxygenated blood and any nutrients or drugs from reservoir 30 flow not only to the heart, but also to the 10 centimeters of the coronary sinus between the catheter tip end and the balloon.

Figure 6:
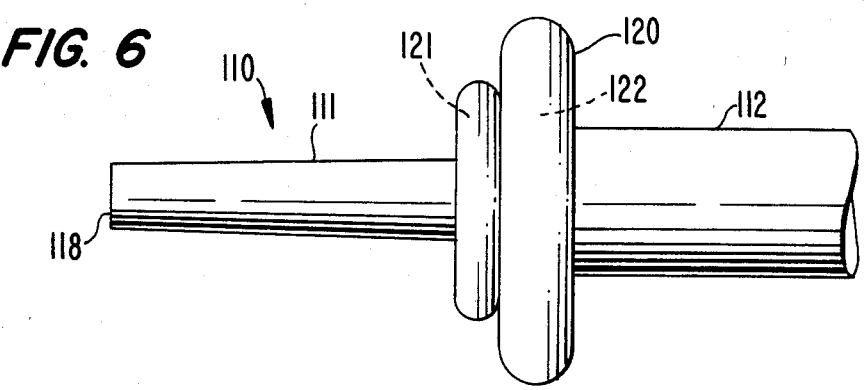
FIG. 6 shows a catheter and balloon for use in another embodiment of the retrograde coronary sinus perfusion device of this invention.

The RCSP device and method of this invention can be made "global" to provide oxygenated blood and nutrients to almost the entire heart, including the portions of the coronary sinus not treated by the system in FIGS. 2-4, and to vasculature connected to those portions of the coronary sinus. FIG. 6 shows an embodiment of a catheter and balloon for a global RCSP device of this invention.

Catheter 110 in FIG. 6 is a double lumen catheter which includes narrow portion 111 and wide portion 112. Catheter 110 also has a slight taper along portion 111 down to tip end 118 which end is inserted into the coronary sinus.

Figure 6A:
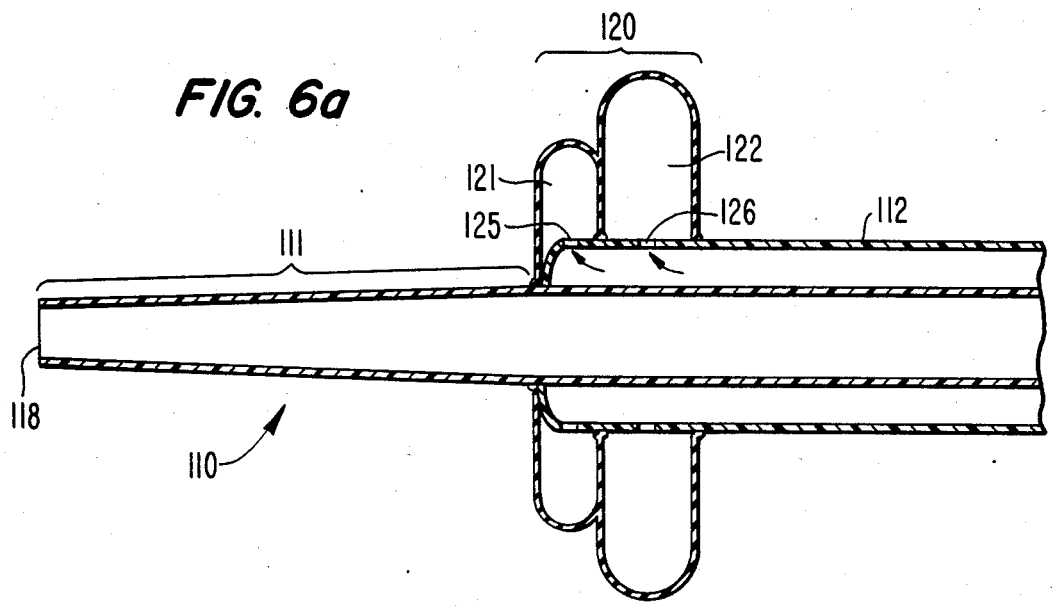
FIG. 6a shows a different view of the catheter and balloon in FIG. 6.

Double compartment balloon 120 includes two compartments 121 and 122. FIG. 6a shows compartments 121 and 122 viewed lengthwise along catheter 110. Balloon 120 sits on catheter 110 where portions 111 and 112 meet. Holes 125 and 126 in catheter 110 provide a gas flow path from one of the lumens of catheter 110 into balloon 120 in the same manner as the RCSP device in FIGS. 2-4.

When catheter 110 is inserted into the coronary sinus, the coronary sinus valve, also called the thebesian valve, lies between compartments 121 and 122. Balloon compartment 121, which lies on catheter 110 closer to tip end 118 than compartment 122, blocks the coronary sinus completely when the balloon is inflated.

Balloon compartment 122 is larger than compartment 121. When inflated, compartment 122 presses against the coronary sinus ostia to ensure that no blood flows out of that opening.

The timing of balloon 120's inflation is as shown in FIG. 5. Blood is constantly provided through a central large lumen as in the RCSP device shown in FIGS. 2-4. In operation, pump 50 inflates balloon 120 slightly before the end of systolic contraction. Balloon 120 and hole 125 are placed on catheter 110 such that when gas flows into balloon 120, compartment 121 inflates before compartment 122. The amount of delay between the compartments' inflating depends on the sizes of the compartments, on the cross-sectional areas of holes 125 and 126, and on the volume and cross-sectional area of the gas carrying lumen of catheter 110. The inflation pressure of the balloon is set to the maximum set pressure of the blood, for example 50 mm Hg, for the reasons described earlier with regard to the embodiment of the invention in FIGS. 2-4.

When inflated, balloon 120 seals off the entire coronary sinus to provide oxygenated blood and nutrients to the entire heart. This global system maximizes retrograde flow because of the elimination of venous "leakage paths" which exist with a non-global system. The fluid-tight seal achieved with the global RCSP device of this invention increases the pressure of the retrograde blood flow.

Figure 7:
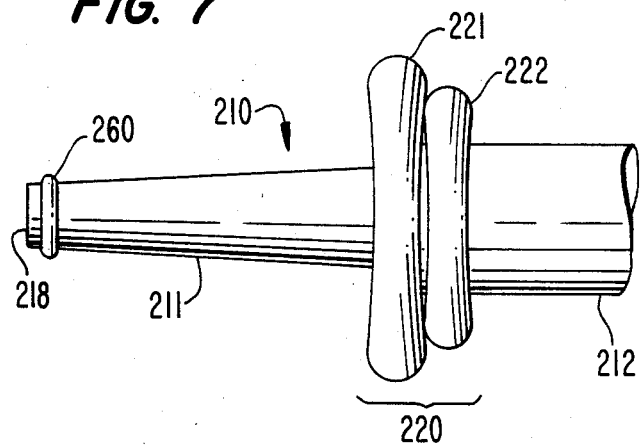
FIG. 7 shows a catheter and balloon for use in another embodiment of the retrograde coronary sinus perfusion device of this invention.

Another embodiment of a catheter which can be used with a global RCSP device according to this invention is shown in FIG. 7. In this embodiment, triple lumen catheter 210 comprises a smaller tapered portion 211 and a larger portion 212 just as in catheter 110. One lumen of catheter 210 provides blood flow, another lumen of catheter 210 directs gas into positioning balloon 260 and balloon 221, and the third lumen directs gas into balloon 222.

Positioning balloon 260 is located on catheter 210 between tip end 218 and balloon 220 and remains inflated during the operation of the RCSP device to prevent catheter 210 from slipping out of the sinus during operation. Balloon 260 is shaped to avoid complete blockage of venous flow from the coronary sinus. The shape of balloon 260 can also be seen in FIG. 7a which is a view from tip end 218 along catheter 210.

Figure 7A:
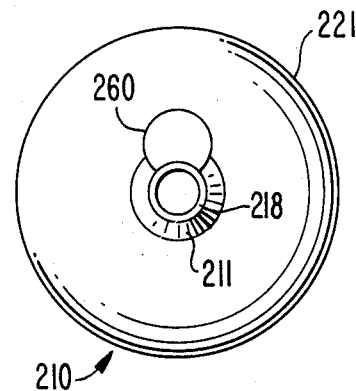
FIG. 7a shows a different view of the catheter and balloon in FIG. 7.

Balloon 220 includes compartments 221 and 222. Compartment 221, which is the closer of the two compartments to tip end 218 of catheter 210, lies just outside the coronary sinus when catheter 210 is properly placed. Compartment 221 is doughnut-shaped and compartment 221's shape is seen in FIG. 7a.

Compartment 221 and 260 are inflated to a set pressure that is slightly higher than the venous pressure of the coronary sinus. During systole, the coronary sinus flow will bend balloon compartment 221 backwards to allow blood drainage from the heart. Just before the end of systole, pump 50 inflates balloon 222 to the maximum coronary sinus pressure. This forces balloon 221 against the coronary sinus opening, thereby completely blocking the coronary sinus drainage.

It will be apparent to those skilled in the art that variations and modifications can be made in the RCSP device and method of this invention. For example, balloon 260 can be replaced with a curved portion of the catheter to secure the catheter's position in the coronary sinus. The invention in its broader aspects is not limited to the specific details, representative methods and apparatus and illustrative examples shown and described, and departure from such details does not necessarily entail departure from the spirit or scope of the general inventive concept.

What is claimed is:

1. A retrograde coronary sinus perfusion device for a patient comprising:

a multiple lumen catheter, a portion of which is to be inserted into the coronary sinus of said patient's heart, said catheter including first and second lumens and a tip end which is inserted into the coronary sinus;

a ballon surrounding said catheter at a distance from said multiple lumen catheter tip end preset to at least substantially the length of said catheter portion to be inserted into the coronary sinus, said multiple lumen catheter portion including a flow path between said balloon and said first lumen so that gas in said first lumen may inflate said ballon;

a reservoir of blood coupled to a distal end of said second lumen of said multiple lumen catheter opposite to said tip end, said reservoir including means for providing a supply of blood into the coronary sinus from said second lumen at a relatively constant pressure, said blood supply providing means including
  entrance means for allowing blood to enter said reservoir, and
  a ball float valve positioned proximate said entrance means to keep the level of blood in said reservoir relatively constant by controlling the supply of blood into said reservoir; and
a balloon pump coupled to said first lumen to force gas into said first lumen at a rate synchronized with the pulse rate of said heart.

2. The device of claim 1 further including a supply catheter connected between an artery of said patient and said reservoir to supply blood to said reservoir.

3. The device of claim 2 further including a pump coupled to said supply catheter to pump blood from said artery to said reservoir through said catheter.

4. The device of claim 1 wherein said multiple lumen catheter is tapered downward from said balloon to said tip end.

5. The device of claim 1 wherein said balloon pump sets the pressure in said balloon approximately equal to the pressure from said reservoir.

6. The device of claim 1 wherein said balloon is located on said catheter to coincide with the valve of said coronary sinus when said catheter is properly inserted into said sinus.

7. A retrograde coronary perfusion device for a patient comprising:
  a multiple lumen catheter, a portion of which is to be inserted into the coronary sinus of said patient's heart, said catheter including first and second lumens and a tip end which is inserted into the coronary sinus;
  a two-chambered balloon surrounding said multiple lumen catheter at a distance from said tip end approximately equal to the portion of said multiple lumen catheter to be inserted into the coronary sinus such that said balloon and the valve of said coronary sinus coincide when said catheter is properly inserted in said sinus, said multiple lumen catheter containing a flow path between said balloon and said first lumen so that gas in said first lumen may inflate said balloon;
  a reservoir of blood coupled to a distal end of said second lumen of said multiple lumen catheter opposite to said tip end, said reservoir including means for providing a supply of blood into the coronary sinus from said second lumen at a relatively constant pressure, said blood supply providing means including
    entrance means for allowing blood to enter said reservoir, and
    a ball float valve positioned proximate said entrance means to keep the level of blood in said reservoir relatively constant by controlling the supply of blood to said reservoir; and
  a balloon pump coupled to said first lumen to force gas into said first lumen at a rate synchronized with the pulse rate of said heart.

8. The device of claim 7 wherein a first chamber of said two-chambered balloon is located closer to said tip end of said multiple lumen catheter than a second chamber of said two-chambered balloon and wherein said first and second chambers are constructed such that when gas is supplied from said first lumen, said first chamber inflates before said second chamber inflates.

9. The device of claim 7 wherein a first chamber of said two-chambered balloon is located closer to said tip end of said multiple lumen catheter than a second chamber, said first chamber having a second elasticity and including means for pushing said first balloon toward said tip end when said second chamber inflates.

10. The device of claim 7 further including means on said catheter for fixing said multiple lumen catheter in said coronary sinus.

11. The device of claim 10 where in said fixing means includes a positioning balloon on said multiple lumen catheter between said tip end and said two-chambered balloon, and wherein said multiple lumen catheter includes a third lumen and a flow path between said positioning balloon and said third lumen.

12. A method of retrograde coronary sinus perfusion for a patent comprising the steps of:
  inserting a portion of a multiple lumen catheter, tip end first, into the coronary sinus of the patient's heart;
  providing blood into the coronary sinus at a relatively constant pressure from an external reservoir of blood;
  maintaining the level of blood in said reservoir relatively constant using a ball float valve; and
  inflating, at a rate synchronized with the pulse rate of said heart, a balloon surrounding the multiple lumen catheter at a distance from said tip end preset to the length of said catheter portion inserted in said coronary sinus.

13. The method in claim 12 further including the step of pumping blood from an artery of said patient into said reservoir.

14. The method in claim 15 wherein said blood pumping step includes the step of using an externally-controlled pump to pump blood to said reservoir.

15. The method of claim 14 wherein said inflating step includes the step of inflating said balloon to the pressure on said blood from said reservoir.

16. The method in claim 14 wherein said inflating step includes the step of completely blocking the coronary sinus when said balloon is inflated.

17. The method of claim 16 wherein said inflating step includes the step of inflating a two-chambered balloon positioned adjacent said coronary sinus valve.

18. The method of claim 17 wherein said two-chambered balloon inflating step includes the steps of inflating a first chamber of said two-chambered balloon before a second chamber of said two chambered balloon, said first chamber being located closer to said tip end than said second chamber.

19. The method of claim 17 wherein said two-chambered balloon inflating step includes the steps of maintaining a first chamber of said two-chambered balloon inflated while said multiple lumen catheter is inserted into said coronary sinus, and inflating a second chamber of said two-chambered balloon in synchronism with said heart rate so, when inflated, said second chamber presses against said first chamber.

20. The method of claim 12 further including the step of fixing said multiple lumen catheter in said coronary sinus by inflating a positioning ballon.

* * * * *